United States Patent [19]

Müller

[11] 4,017,565
[45] Apr. 12, 1977

[54] DEVICE FOR ADMIXING A GASEOUS AND A LIQUID PHASE

[76] Inventor: Hans Müller, Im Almendli, Erlenbach, Zurich, Switzerland

[22] Filed: Feb. 24, 1976

[21] Appl. No.: 661,026

Related U.S. Application Data

[63] Continuation of Ser. No. 487,808, July 11, 1974, abandoned.

[30] Foreign Application Priority Data

July 13, 1973  Switzerland ............... 10300/73

[52] U.S. Cl. .................. 261/36 R; 195/142; 195/143; 261/93; 261/123; 261/DIG. 75
[51] Int. Cl.² ................ B01F 3/04; C12B 1/16
[58] Field of Search ............ 261/36 R, 77, 87, 93, 261/123, 124, DIG. 75; 195/109, 142–144

[56] References Cited

UNITED STATES PATENTS

| | | | |
|---|---|---|---|
| 2,293,183 | 8/1942 | Walker | 261/93 |
| 3,201,327 | 8/1965 | Beck | 261/36 R X |
| 3,462,132 | 8/1969 | Kaelin | 261/87 |
| 3,572,661 | 3/1971 | Muller | 261/93 X |
| 3,625,834 | 12/1971 | Muller | 261/93 X |
| 3,650,950 | 3/1972 | White | 261/87 X |
| 3,776,531 | 12/1973 | Ebner et al. | 261/87 |
| 3,846,516 | 11/1974 | Carlson | 261/87 |

FOREIGN PATENTS OR APPLICATIONS

| | | | |
|---|---|---|---|
| 48,730 | 4/1934 | Denmark | 261/93 |
| 2,042,791 | 3/1971 | Germany | 261/93 |
| 562,894 | 7/1944 | United Kingdom | 261/93 |
| 548,664 | 10/1942 | United Kingdom | 261/93 |

Primary Examiner—Tim R. Miles
Assistant Examiner—Richard L. Chiesa
Attorney, Agent, or Firm—Michael J. Striker

[57] ABSTRACT

An upright vessel for the liquid phase has a cylindrical baffle located in it extending upwardly from the lower region of the vessel. The baffle has a lower open end at which an impeller is located and an upper open end which is formed with a constriction. A member provided with passages through which the gaseous phase is discharged, is located in the constriction so that the passages discharge the gaseous phase at the narrowest cross-section of an annular clearance formed between the constriction and the member.

7 Claims, 1 Drawing Figure

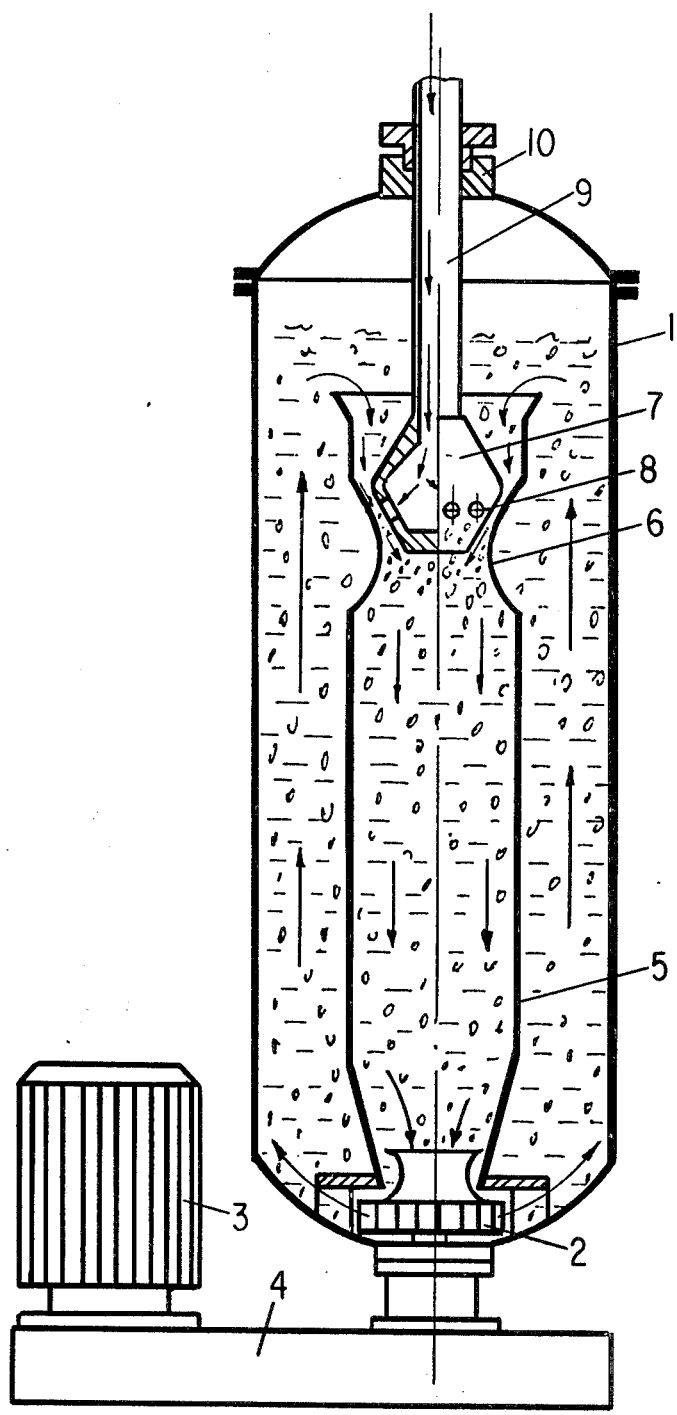

as a continuation of application Ser. No. 487,808, filed July 11, 1974, now abandoned.

DEVICE FOR ADMIXING A GASEOUS AND A LIQUID PHASE

This is a continuation of application Ser. No. 487,808, filed July 11, 1974, now abandoned.

BACKGROUND OF THE INVENTION

The present invention relates generally to a device for admixing liquid and gaseous phases, and more particularly to a device for mixing a gaseous phase into a liquid phase which is particularly suitable for aerobic microbiological processes and the like.

Devices of the type in question are already known. They have vessels which accommodate the liquid phase, and it is known to provide a tubular guide baffle in such a vessel, forming the guide baffle with apertures in its circumference, and providing adjacent one end of the guide baffle an impeller which draws the liquid phase through the openings and into the guide baffle from the space surrounding the same. The gaseous phase is admitted into the vessel, and as it is drawn through the openings into the guide baffle together with the liquid phase, the two become mixed.

There are circumstances in which the vessel of such an apparatus must be tall and substantially cylindrical but can have only a relatively small diameter. One of these is the fact that frequently space is at a premium and larger-diameter vessels cannot be accommodated. If such a relatively high vessel is used, then the hydrostatic pressure of the liquid phase in the filled vessel is considerable in the lower region thereof, due to the column of liquid located in the upper regions. This pressure can be so great that the gaseous phase must be forcibly pressed into the interior of the vessel by means of compressors. If the vessel is large, and therefore requires substantial quantities of the gaseous phase, such installations are very expensive both as to their construction and operation, and therefore quite frequently cannot be operated economically.

SUMMARY OF THE INVENTION

It is, therefore, a general object of the invention to overcome the disadvantages of the prior art.

More particularly, it is an object of the present invention to provide an improved device for admixing gaseous and liquid phases, which is not possessed of the aforementioned disadvantages.

Another object of the invention is to provide such a device which is simpler to construct and to operate than those known from the prior art.

A further object of the invention is to provide such a device wherein the pressure required to force the gaseous phase into the interior of the device is substantially reduced over those of the prior art, so that instead of compressors it is possible to use fans or other low-pressure blowers which are less expensive to construct and to operate.

In keeping with the above objects and with others which will become apparent hereafter, one feature of the invention resides, in a device for admixing a gaseous and a liquid phase particularly in a reaction vessel or a fermentor, in a combination which comprises an upright vessel for the liquid phase, and a substantially cylindrical baffle extending in the vessel upwardly from a lower region thereof. The baffle has a lower open end and an upper end provided with a constriction which forms a throat. Impeller means is provided in the region of the lower open end for impelling a flow of the liquid phase through the baffle. Admitting means is provided for admitting the gaseous phase into the baffle in the region of the throat thereof.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

The single FIGURE is a somewhat diagrammatic axial section through an embodiment of the invention.

DESCRIPTION OF THE PREFERRED EMBODIMENTS

Referring to the drawing in detail, it will be seen that in the exemplary embodiment which has been illustrated a vessel 1 is of cylindrical shape and has an upright orientation. In the region of the bottom of the vessel there is located in the interior an impeller 2 which axially draws the contents in terms of liquid and gaseous phase, and which throws the contents in radial direction. In other words, the contents are drawn downwardly in the vessel 1, and are expelled in radial direction. An electromotor 3 is provided which drives the impeller 2 via a transmission 4.

Located within the vessel 1, extending axially thereof in upright direction and having its lower open end located above the impeller 2 is a tubular guide baffle 5 which extends into the upper region of the vessel 1 and which has a constriction 6 at its upper end. Located in this upper end is a gas-admitting body 7 which is constructed as a hollow double-conical member and which is mounted on a hollow supply tube 9, which is in turn so mounted that it can be shifted vertically, that is axially of the baffle 5. The body 7 defines with the throat of the constriction 6 an annular gap the cross-section of which can be varied when the body 7 and the tube 9 are shifted in axial direction. The body 7 has gas outlet openings 8 which are located in a common plane transverse to the elongation of a body 7. The tube 9 is mounted in the stuffing box 10 which serves to seal the upper end of the vessel 1 and also to hold the tube 9 for such shiftable displacement.

The liquid phase which is to have a gaseous phase admixed with it, and which may be for instance a nutrient medium with microorganisms, is admitted into the vessel 1 either batch-wise or continuously, and a gaseous phase — such as air — is blown through the tube 9. When the impeller 2 is operated, the liquid phase is drawn axially in downward direction through the baffle 5, entering the latter at the upper open end, and is expelled radially at the bottom end thereof. It therefore can move upwardly outside the guide baffle 5, whereas inside the guide baffle 5 it moves downwardly. Depending upon the axial position of the body 7, the latter defines with the wall bounding the constriction 6 of the guide baffle 5 an annular gap of greater or lesser cross-section, in which the liquid phase reaches its highest flow speed, so that a suction is exerted at the location at which the openings 8 are provided. Since the body 7 is located in the upper region of the vessel 1, the hydrostatic pressure which heretofore was objectionable in the prior art cannot act to prevent the ready introduction of the gaseous phase, especially as there is in this region an underpressure resulting from the Venturi effect of the flow of the liquid phase through the throat of the constriction.

The construction according to the present invention overcomes fully the disadvantages of the prior art, and in most instances it is actually not necessary to provide any blower at all, because it has been found that in most instances the suction effect exerted by the liquid phase which rushes through the annular gap where the constriction 6 forms the throat, is sufficient to draw air or other gaseous medium through the openings, the body 7 and the tube 9. This substantially increases the economy of operation of the device, since no energy is required for a blower or the like to blow the gaseous phase into the vessel 1, and it also reduces the expenses of constructing the device since no blower or similar element need be provided.

It will be understood that each of the elements described above, or two or more together, may also find a useful application in other types of constructions differing from the types described above.

While the invention has been illustrated and described as embodied in a device for admixing a gaseous and a liquid phase, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. In a device for admixing a liquid and a gaseous medium, particularly in a reaction vessel or a fermentor, a combination comprising an upright vessel for the liquid medium; a substantially cylindrical tubular baffle extending in said vessel upwardly from a lower region thereof, said cylindrical tubular baffle having a lower open end and an upper end portion provided with a constricted region which bounds a throat; admitting means for admitting the gaseous medium into said cylindrical tubular baffle in the region of said throat, said admitting means including a substantially barrel-shaped elongated hollow gas-admitting body located in said upper end portion of said cylindrical tubular baffle coaxially with said throat, and defining a substantially Venturi-shaped annular gap in said throat with said constricted region, said hollow gas-admitting body having an interior containing a replenishable volume of the gaseous medium and a plurality of small-sized gas outlet openings penetrating said hollow gas-admitting body in a common plane which extends normal to the longitudinal axis of said hollow gas-admitting body, said openings being directed outwardly of said hollow gas-admitting body so as to communicate said interior of the latter with said Venturi-shaped annular gap to thereby supply the gaseous medium into said Venturi-shaped annular gap in direction toward said constricted region of said cylindrical tubular baffle; and impeller means located in the region of said lower open end of said cylindrical tubular baffle and operative for drawing the liquid medium downwardly through said cylindrical tubular baffle and through said annular gap so that underpressure caused by Venturi effect develops in the liquid medium flowing through said Venturi-shaped annular gap and draws the gaseous medium in form of a fine dispersion through said plurality of small-sized gas outlet openings into said Venturi-shaped annular gap.

2. A combination as defined in claim 1; and further comprising means mounting said body for limited axial displacement relative to said baffle.

3. A combination as defined in claim 1, wherein said admitting means further comprises an inlet tube communicating with the interior of said body and extending to the exterior of said vessel.

4. A combination as defined in claim 3, wherein said body is carried by said tube; and further comprising means mounting said tube for a limited displacement of the same and thereby of said body in direction axially of said baffle.

5. A combination as defined in claim 1, wherein said upright vessel has a bottom wall portion; and wherein said impeller means includes a drive shaft passing through said bottom wall portion, and an impeller mounted on said drive shaft so as to share the rotation thereof.

6. A combination as defined in claim 1, wherein said upright vessel has a bottom wall portion having an inner concave surface; and wherein said impeller means impels the contents of the vessel radially thereof and along said inner concave surface.

7. A combination as defined in claim 1, wherein said baffle has a lower end portion converging toward said open end, and a substantially cylindrical portion intermediate said constricted region and said lower end portion.

* * * * *